(12) United States Patent
McCollough

(10) Patent No.: US 9,486,293 B2
(45) Date of Patent: Nov. 8, 2016

(54) SURGICAL DRAPE KIT

(75) Inventor: Andrye McCollough, Oak Ridge, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/097,784

(22) Filed: Apr. 29, 2011

(65) Prior Publication Data

US 2011/0284012 A1 Nov. 24, 2011

Related U.S. Application Data

(60) Provisional application No. 61/329,192, filed on Apr. 29, 2010.

(51) Int. Cl.
*A61B 19/08* (2006.01)
*A61B 17/00* (2006.01)

(52) U.S. Cl.
CPC ............... *A61B 46/23* (2016.02); *A61B 46/00* (2016.02); *A61B 50/00* (2016.02); *A61B 90/90* (2016.02); *A61B 2017/00818* (2013.01); *A61B 2046/234* (2016.02); *A61B 2046/236* (2016.02)

(58) Field of Classification Search
USPC ....... 128/846, 849, 850, 851, 852, 853, 854, 128/855; 220/528; 206/438
See application file for complete search history.

(56) References Cited

U.S. PATENT DOCUMENTS

| 4,466,430 | A | 8/1984 | Shultz | |
|---|---|---|---|---|
| 4,476,860 | A * | 10/1984 | Collins et al. | 128/853 |
| 5,036,866 | A | 8/1991 | Eldrige, Jr. et al. | |
| 5,074,316 | A | 12/1991 | Dowdy | |
| 5,074,846 | A | 12/1991 | Clegg et al. | |
| 5,082,111 | A | 1/1992 | Corbitt, Jr. et al. | |
| 5,097,963 | A | 3/1992 | Chernosky et al. | |
| 5,170,804 | A * | 12/1992 | Glassman | 128/849 |
| 5,464,025 | A | 11/1995 | Charles et al. | |
| 5,778,890 | A | 7/1998 | Löfgren et al. | |
| 5,901,706 | A | 5/1999 | Griesbach et al. | |
| 5,931,303 | A | 8/1999 | Salvadori | |
| 6,213,124 | B1 * | 4/2001 | Butterworth | 128/853 |
| 6,234,310 | B1 | 5/2001 | Goldhaber | |
| 6,694,981 | B2 * | 2/2004 | Gingles et al. | 128/849 |

(Continued)

FOREIGN PATENT DOCUMENTS

FR 2650501 2/1991
JP 1996-047499 2/1996

(Continued)

OTHER PUBLICATIONS

International Search Report dated Aug. 23, 2011, issued in related International Patent Application No. PCT/US2011/034283.
Percutaneous Endoscopic Gastrostomy Systems—FLOW/PEG Pull Technique, Cook, Wilson-Cook Medical GI Endoscopy, 18981/ 0305, pp. 1-6.

(Continued)

*Primary Examiner* — Ophelia A Hawthorne
(74) *Attorney, Agent, or Firm* — Brinks Gilson & Lione

(57) ABSTRACT

A surgical drape kit for performing a surgical procedure includes a surgical drape having a fenestration site; a plurality of containers attached to the surgical drape; and a plurality of components used to perform a surgical procedure. The containers are attached to the surgical drape around a perimeter of the fenestration site. Each container includes at least one component. Disposition of the components inside the containers is determined by sequential steps of the surgical procedure.

18 Claims, 7 Drawing Sheets

(56) References Cited

U.S. PATENT DOCUMENTS

| | | | |
|---|---|---|---|
| 6,764,308 B1* | 7/2004 | Broberg et al. | 433/157 |
| 6,808,519 B2 | 10/2004 | Fanelli et al. | |
| 7,293,654 B1 | 11/2007 | Wilson, Jr. et al. | |
| 7,401,703 B2* | 7/2008 | McMichael et al. | 206/570 |
| 7,997,408 B2* | 8/2011 | Peck | 206/438 |
| 2004/0118410 A1* | 6/2004 | Griesbach et al. | 128/852 |
| 2006/0169290 A1 | 8/2006 | Harris et al. | |
| 2007/0107130 A1 | 5/2007 | Elhabashy | |
| 2007/0235038 A1 | 10/2007 | Alinsod et al. | |
| 2008/0283534 A1* | 11/2008 | Paz | 220/528 |
| 2010/0300459 A1* | 12/2010 | Lair | 128/853 |

FOREIGN PATENT DOCUMENTS

| | | |
|---|---|---|
| JP | 2002-136597 | 5/2002 |
| JP | 2002-302217 | 10/2002 |
| JP | 2003-512126 | 4/2003 |
| JP | 2006-511285 | 4/2006 |
| WO | WO 01/30258 A1 | 5/2001 |
| WO | WO 2004/060184 A1 | 7/2004 |

OTHER PUBLICATIONS

Percutaneous Endoscopic Gastrostomy Systems—FLOW-J/PEG-J Gastro-Jejunal Feeding Tube, Cook, Wilson-Cook Medical GI Endoscopy, 18879/0105, pp. 1-5.
Percutaneous Endoscopic Gastrostomy Systems—FLOW/PEG Push Technique, Cook, Wilson-Cook Medical GI Endoscopy, 18897/0205, pp. 1-6.
EndoVive Safety PEG Kits, Boston Scientific Corporation, Natick, MA 2009.
EndoVive, Low Profile PEGs, Boston Scientific Corporation, Natick, MA 2009.
EndoVive, Standard PEGs, Boston Scientific Corporation, Natick, MA 2009.
Examiner's Report for corresponding Canadian Patent Application No. 2,797,261 dated Oct. 14, 2014.
Japanese Office Action for corresponding Japanese Application No. 2013-508245 including translation dated Nov. 26, 2014.
Office Action in corresponding Canadian Application No. 2,797,261, dated Mar. 29, 2016, 4 pages.
Examiner's Report for corresponding Canadian Application No. 2,797,261 mailed Jun. 17, 2015.

* cited by examiner

SURGICAL DRAPE KIT

PRIORITY CLAIM

This application claims the benefit of U.S. Provisional Application 61/329,192, entitled "Surgical Drape Kit," filed Apr. 29, 2010, the disclosure of which is hereby incorporated by reference in its entirety.

FIELD OF THE INVENTION

The present invention relates generally to surgical kits, and more particularly to an improved packaging and arrangement of surgical drape kits.

BACKGROUND OF THE INVENTION

Surgical drapes are used to cover a patient during a surgical procedure in order to create and maintain a sterile environment about the surgical site. Surgical drapes commonly have an opening, also known as a "fenestration," through which the surgical procedure is performed. An adhesive material may be attached to the periphery of the drape material so that the drape can be held in place around the surgical site and so that blood will not pass between the drape and the patient's body. It is often desirable that the surgical drapes are made with an absorbent material to absorb blood and other fluids during surgery.

Surgical drapes may be part of a surgical kit for a given procedure. The surgical kit contains medical instruments, devices, and other materials that will be used in the procedure. As a surgical kit, the medical devices, instruments, and other materials are provided to an end user, such as a surgeon, as prepackaged items. The user will use the contents of the kit as needed during the procedure. Often times, the medical devices and instruments comprising the kit are disposed after the procedure is done. Hence, the devices in the kit are supplied to users sterile and are typically intended for single use only.

An example of a procedure that makes use of a surgical kit is percutaneous endoscopic gastrostomy (PEG). PEG is an endoscopic procedure for placing a feeding tube into a stomach of a patient. Two techniques for performing the PEG procedure are the push technique and the pull technique. Accordingly, the contents of the PEG kits depend on the PEG technique being used.

A PEG kit may include: a silicone feeding tube, a wire guide if the push technique is being used, an insertion wire if the pull technique is being used, a syringe, at least one needle (preferably there are two needles—a 22 gauge needle and a 25 gauge needle), a scalpel, a needle cannula, lidocaine hydrochloride (e.g., Xylocaine® 1%), swab sticks (e.g., ChloraPrep® Triple Swabsticks), povidone ointment, water soluble lubricant, a bolster, at least one twist lock, at least one cable tie, scissors, a universal adapter, a bolus adapter, feeding adapters (if the kit is sold internationally), gauze pads, a surgical drape, and a cold snare.

The medical devices and instruments used in the PEG procedure may be received for use in the form of a PEG kit. An example of a PEG kit is Wilson-Cook Medical, Inc.'s PEG-24® kit. The PEG-24® kit is packaged in a thermoformed plastic container. A cover is attached to a lid of the thermoformed container using an adhesive material. The components of the PEG-24® kit located inside the thermoformed container are accessed by peeling the cover off of the lid.

The PEG-24® kit includes a prep tray that is made of a thermoplastic material. Securely fastened to the prep tray are a syringe, a twenty-two gauge needle, a twenty-five gauge needle, a scalpel, a needle cannula, and lidocaine hydrochloride (e.g., Xylocaine® 1%). Loosely placed atop the prep tray are a surgical drape, a wire guide (if the push technique is being used), the insertion wire (if the pull technique is being used), gauze pads, a cold snare, povidone iodine swabs, swab sticks, and water soluble lubricant. Packaged below the prep tray are a bolster kit and a feeding tube. The bolster kit includes a bolster, twist locks, a cable tie, scissors, a universal adapter, and a bolus adapter.

Generally, a surgical kit should be packaged to minimize the likelihood that the items in the kit become contaminated, lost, or damaged. Additionally, the surgical kit should be arranged such that during the procedure the components of the kit are as accessible as possible to a user needing to obtain them. That is, the end user, such as a surgeon, should be able to identify a desired item, obtain the item, and move the item to the surgical site as quickly and as easily as possible.

BRIEF SUMMARY OF THE INVENTION

The present invention provides an improved packaging and arrangement of surgical kits having a surgical drape that are used to perform a surgical procedure on a patient. The invention is directed to a surgical drape kit that comprises a surgical drape having a fenestration site, a plurality of containers attached to the surgical drape, and a plurality of components used to perform the surgical procedure, wherein each of the containers includes at least one of the components disposed therein, wherein the plurality of components disposed inside each of the containers is determined by sequential steps of the surgical procedure, and wherein the containers are attached to the surgical drape around a perimeter of the fenestration site.

One surgical procedure that may use a surgical kit having a surgical drape is percutaneous endoscopic gastrostomy (PEG). The PEG procedure may be divided into individual steps, including making an incision, inserting a wire into the patient for enabling insertion of a feeding tube into the patient, inserting the feeding tube into the patient, applying a bolster to the feeding tube, and attaching an adapter to the feeding tube. The determination for disposing the plurality of components inside the containers is based on these steps for performing the PEG procedure.

In a preferred embodiment, the surgical drape kit comprises four containers. A first container includes components that relate to the step of making an incision disposed therein. A second container includes components that relate to the step of inserting a wire for enabling insertion of a feeding tube disposed therein. A third container includes components that relate to the step of inserting the feeding tube disposed therein. A fourth container includes components that relate to the step of applying a bolster to the feeding tube disposed therein, and components that relate to the step of attaching an adapter to the feeding tube disposed therein.

The components that relate to the step of making an incision include a scalpel, and may further include a syringe, a twenty-two gauge needle, and twenty-five gauge needle, and a container of lidocaine hydrochloride. The components that relate to the step of inserting a wire to enable insertion of a feeding tube include a wire guide when a push technique is used to perform the PEG procedure, or an insertion wire having a looped end when a pull technique is used to perform the PEG procedure, and may further include a cold snare, and a needle cannula. The components that relate to the step of inserting the feeding tube include the feeding tube, and may further include at least one gauze pad, and at least one package of water soluble lubricant. The components that relate to applying a bolster to the feeding tube include a bolster, and may further include at least one package of povidone-iodine ointment. The components that relate to attaching an adapter to the feeding tube include at least one of a universal adapter and a bolus adapter, and may further include forceps, scissors, at least one cable tie, at least one twist lock tie, and a feeding tube clamp.

DETAILED DESCRIPTION OF THE INVENTION

Figure 1:
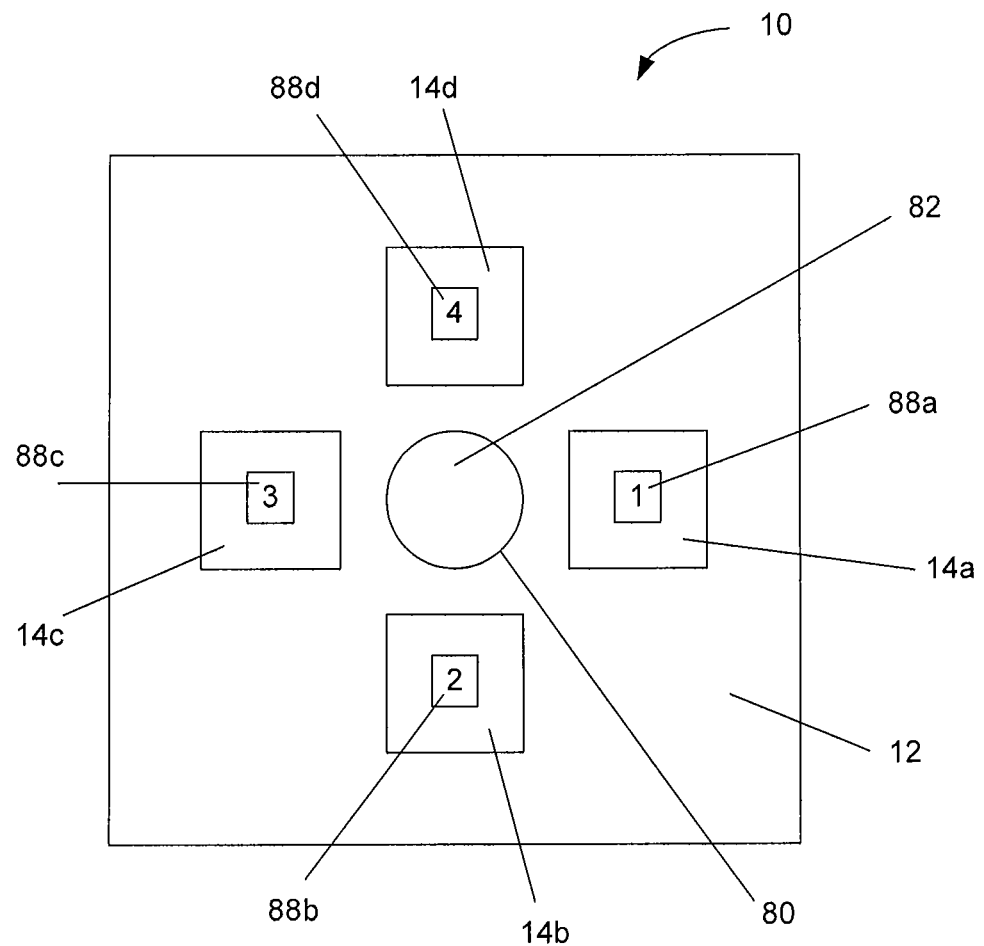
FIG. 1 is a top view of the preferred embodiment of the surgical drape kit, and illustrates four containers sequentially attached to the surgical drape around the perimeter of the fenestration site in a clockwise configuration.

The present invention is directed to a surgical drape kit 10 comprising a surgical drape 12, a plurality of containers 14 attached to the surgical drape 12, and a plurality of components 18-54 used to perform the surgical procedure, wherein each of the containers 14 includes at least one of the components 18-54 disposed therein, wherein the components 18-54 disposed inside each of the containers 14 is determined by sequential steps of the surgical procedure, and wherein the containers 14 are attached to the surgical drape 12 around a perimeter 80 of a fenestration site 82 of the surgical drape 12.

The surgical drape kit 10 of the present invention may be used for surgical procedures that makes use of a surgical kit. One example of a surgical procedure that makes use of a surgical kit is a percutaneous endoscopic gastrostomy (PEG) procedure.

Before performing the PEG procedure (the pull or the push technique), a gastroscope is inserted through the mouth and down the esophagus to view the stomach. The stomach is insufflated and the mucosa is examined to make sure the mucosa is free of ulceration. The gastroscope is positioned such that a light of the gastroscope trans-illuminates the desired PEG site. After it is determined that the mucosa is healthy, the PEG procedure begins.

When performing the PEG procedure using the push technique, the PEG site is draped using the surgical drape 12 and local anesthetic is injected into the site. An incision through the skin and subcutaneous tissue is made using a scalpel 26. Prior to making the incision, swab sticks 56 are applied to the incision site. The swab sticks 56 may be used before or after the surgical drape 12 is placed over the patient.

After the incision is made, and while the stomach is insufflated, a needle 30 and a cannula 38 are inserted through the incision and into the stomach. Once in the stomach, the cannula 38 is left in place and the needle 30 is removed.

After removing the needle 30, a tip of a wire guide 18 is inserted through the cannula 38 and into the stomach.

Next, a cold snare 36 is inserted through a channel of the gastroscope. When the cold snare 36 reaches the inside of the stomach, the snare 36 grasps an end of the wire guide 18. While the snare 36 is securely attached to the end of the wire guide 18, the gastroscope and wire guide 18 are removed from the stomach through the patient's mouth, leaving the wire guide 18 protruding from the mouth and the incision site.

Then, a feeding tube 20 is inserted into the patient. The feeding tube 20 comprises a first portion having a dilator tip at a first end, and a second portion having an end cap or a "tulip tip" at a second end. Before being inserted into the patient, the feeding tube 20 is lubricated using water soluble lubricant. After the tube 20 is lubricated, the feeding tube 20, beginning with the dilator tip, is advanced over the wire guide 18 and through the patient's mouth. When the second end meets the cannula 38 in the stomach, the first portion is pushed through an abdominal wall of the stomach. After the first end passes through the abdominal wall, the wire guide 18 is released and the feeding tube 20 and the wire guide 18 are pulled through the abdominal wall.

When the tulip tip enters the mouth, the gastroscope is reintroduced into the patient's mouth in order to view the tulip tip as it is advanced through the esophagus and into the stomach. The first portion is pulled through the abdominal incision, and the tulip tip engages with the abdominal wall. Thereafter, the wire guide 18 is removed.

Next, the bolster 22 is positioned over the feeding tube 20 at the PEG site by placing it over the feeding tube 20 at the first end and sliding it down to the patient's skin. Before sliding the bolster 22 into position, povidone ointment may be applied to bodily tissue at the incision site. After the bolster 22 is engages with the skin surface, an excess portion of the tube 20 is cut using scissors 46. An "X mark" may denote the location at which to cut off the excess portion of the tube 20. A twist lock tie 50 or a cable tie 48 is used to secure the bolster 22 to the tube 20, which prevents future migration of the tube 20 and reduces the need to reposition the tube 20. The scissors 46 may be used to cut off any excess length of the cable tie 48. Finally, the universal adapter 24*a*, bolus adapter 24*b*, or feeding adapters 24*c* are attached to the first portion of the feeding tube 20 at the dilator tip.

Alternatively, when using the pull technique to perform the PEG procedure, the PEG site is draped using the surgical drape 12 and local anesthetic is injected into the site. An incision through the skin and subcutaneous tissue is made using a scalpel 26. Prior to making the incision, swab sticks 56 are applied to the incision site. The swab sticks 56 may be used before or after the surgical drape is placed over the patient.

After the incision is made, and while the stomach is insufflated, a needle 30 and cannula 38 are inserted through the incision and into the stomach. Once in the stomach, the cannula 38 is left in place and the needle 30 is removed.

After removing the needle 30, an insertion wire 18 is inserted through the cannula 38 and into the stomach.

Next, a cold snare 36 is inserted through a channel of the gastroscope and grasps a looped end of the insertion wire 18. Biopsy forceps may be used instead of the cold snare 36. While the cold snare 36 or the biopsy forceps is securely attached to the looped end of the insertion wire 18, the gastroscope and insertion wire 18 are removed from the stomach through the patient's mouth, leaving the looped end of the insertion wire 18 protruding from the mouth and a second end of the insertion wire 18 protruding from the incision site.

Next, the feeding tube 20 is inserted into the patient. In order to insert the feeding tube 22 using the pull technique, a knotless connection is formed between the looped end of the insertion wire 18 protruding from the patient's mouth and a looped end of a wire at the first end of the feeding tube 20. To make the knotless connection, the looped end of the insertion wire 18 is fed through the looped wire of the feeding tube 20, and the tulip tip is then placed through the looped end of the insertion wire 18. Thereafter, the feeding tube 20 is pulled through the looped end of the insertion wire 18. A knotless connection between the insertion wire 18 and the wire of the feeding tube 20 is formed by pulling the looped ends of the wires in opposite directions.

Before the feeding tube 20 is inserted into the patient, the feeding tube 20 is lubricated using the water soluble lubricant. After being lubricated, the feeding tube 20, beginning with the dilator tip, is advanced through the patient's mouth by pulling on the second end of the insertion wire 18 that is protruding from the incision site. The insertion wire 18 is pulled until the first portion protrudes through the abdominal wall.

When the tulip tip enters the mouth, the gastroscope is reintroduced into the patient's mouth in order to view the tulip tip as it is advanced through the esophagus and into the stomach. The first portion is pulled through the abdominal incision, and the tulip tip is brought in contact with the abdominal wall. Thereafter, the insertion wire 18 is removed.

Next, a bolster 22 is positioned over the feeding tube 20 at the PEG site by placing the bolster 22 over the looped wire of the feeding tube 20 at the first end and sliding the bolster 22 down the feeding tube 20 to the patient's skin. Before sliding the bolster into position, povidone ointment may be applied to bodily tissue at the incision site. After the bolster 22 engages with the skin surface, an excess portion of the tube may be cut using scissors 46. An "X mark" may denote the place at which to cut off the excess portion of the tube 20. A twist lock tie 50 or a cable tie 48 may be used to secure the bolster 22 to the tube 20, which prevents future migration of the tube 20 and reduces the need to reposition the tube 20. The scissors 46 may be used to cut off any excess length of the cable tie 48. Thereafter, a universal adapter 24a, a bolus adapter 24b, or feeding adapters 24c are attached to the first portion of the feeding tube 20 at the dilator tip.

Based on the above description, the PEG procedure may be divided into the following steps: making an incision, inserting a wire into the patient for enabling insertion of a feeding tube into the patient, inserting the feeding tube into the patient, applying a bolster to the feeding tube, and attaching an adapter to the feeding tube. An arrangement of the plurality of components 18-54 inside the containers 14 may be based on these steps of the PEG procedure.

FIGS. 1-5 illustrate a preferred embodiment of the surgical drape kit 10 for performing a PEG procedure. As shown in FIG. 1, the surgical drape kit 10 comprises four containers 14 attached to the surgical drape 12. A first container 14a contains components related to the step of the PEG procedure involving making an incision. A second container 14b contains components related to the step of the PEG procedure involving inserting a wire 18 into the patient for enabling insertion of a feeding tube 20 into the patient. When the PEG procedure is performed using a push technique, the wire 18 is a wire guide. When the PEG procedure is performed using a pull technique, the wire 18 is an insertion wire having a looped end. A third container 14c contains components related to the step of the PEG procedure involving inserting the feeding tube 20 into the patient. A fourth container 14d contains components related to a step of the PEG procedure involving applying a bolster 22 to the feeding tube 20 and to the step of the PEG procedure involving adding an adapter 24.

Figure 2:
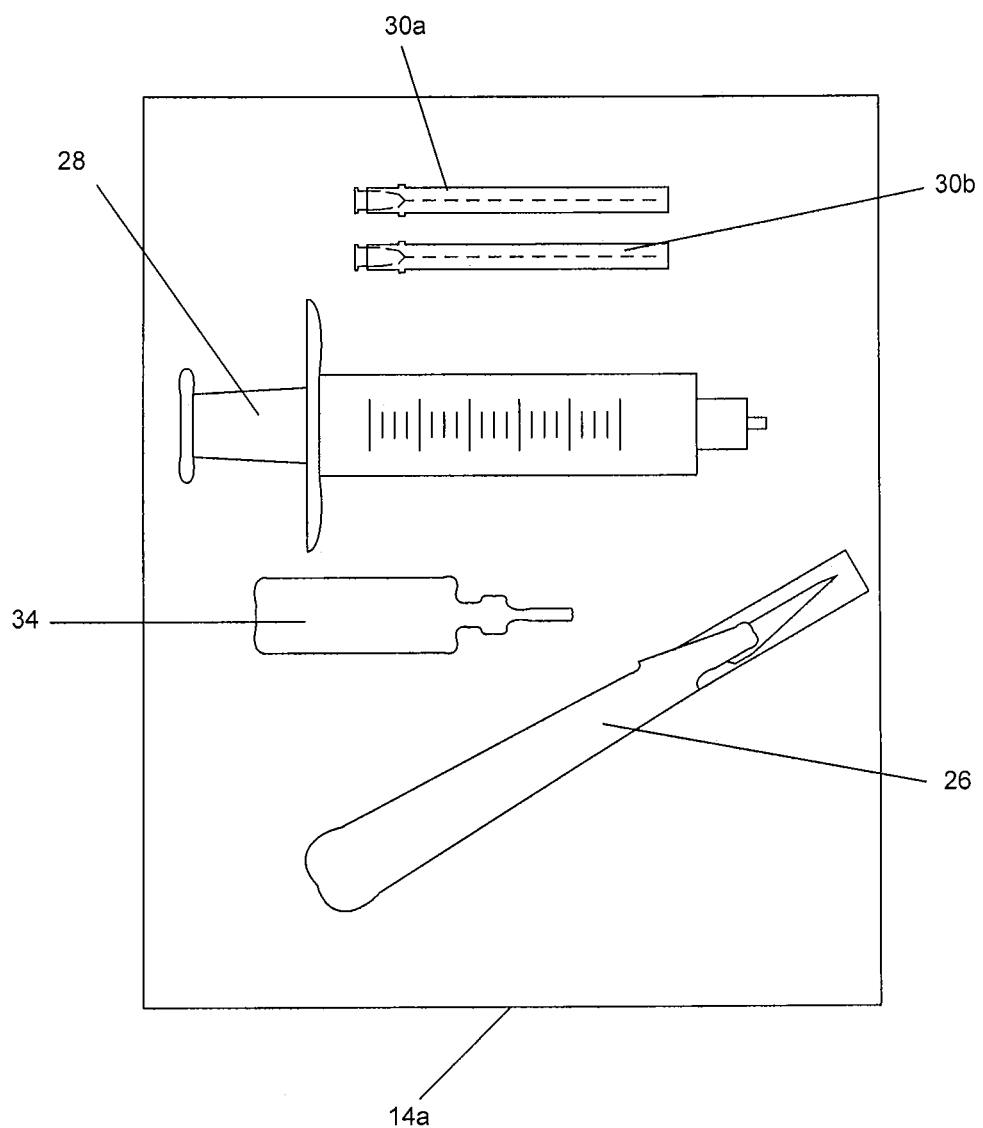
FIG. 2 is a top view of the components inside the first container of the preferred embodiment that relate to the step of making an incision.

As shown in FIG. 2, in the preferred embodiment, the first container 14a may contain a scalpel 26, where the scalpel 26 is preferably a number 11 scalpel; a syringe 28, where the syringe is preferably a six milliliter luer lock syringe; at least one needle 30 having a removable needle casing, where the at least one needle 30 preferably comprises a twenty-two gauge monoject needle 30a, and a twenty-five gauge monoject needle 30b; and a container of lidocaine hydrochloride 34, where the lidocaine hydrochloride 34 is preferably five milliliters of Xylocaine® 1%.

Figure 3:
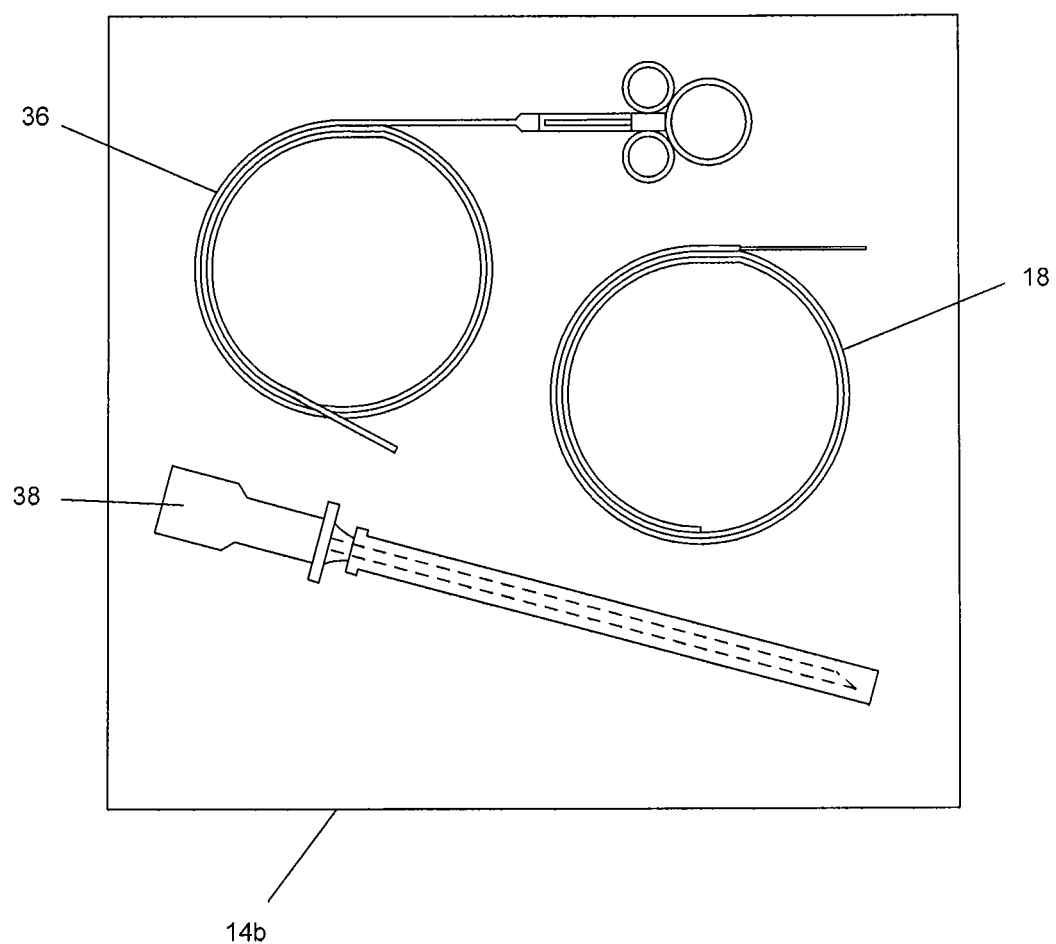
FIG. 3 is a top view of the components inside the second container of the preferred embodiment that relate to the step of inserting the wire into the patient for enabling insertion of the feeding tube into the patient.

As shown in FIG. 3, in the preferred embodiment, the second container 14b may contain the wire 18, where the wire 18 is a wire guide when the push technique is used to perform the PEG procedure, and where the wire 18 is an insertion wire having a looped end when the pull technique is used to perform the PEG procedure; a cold snare 36; and a needle cannula 38.

Figure 4:
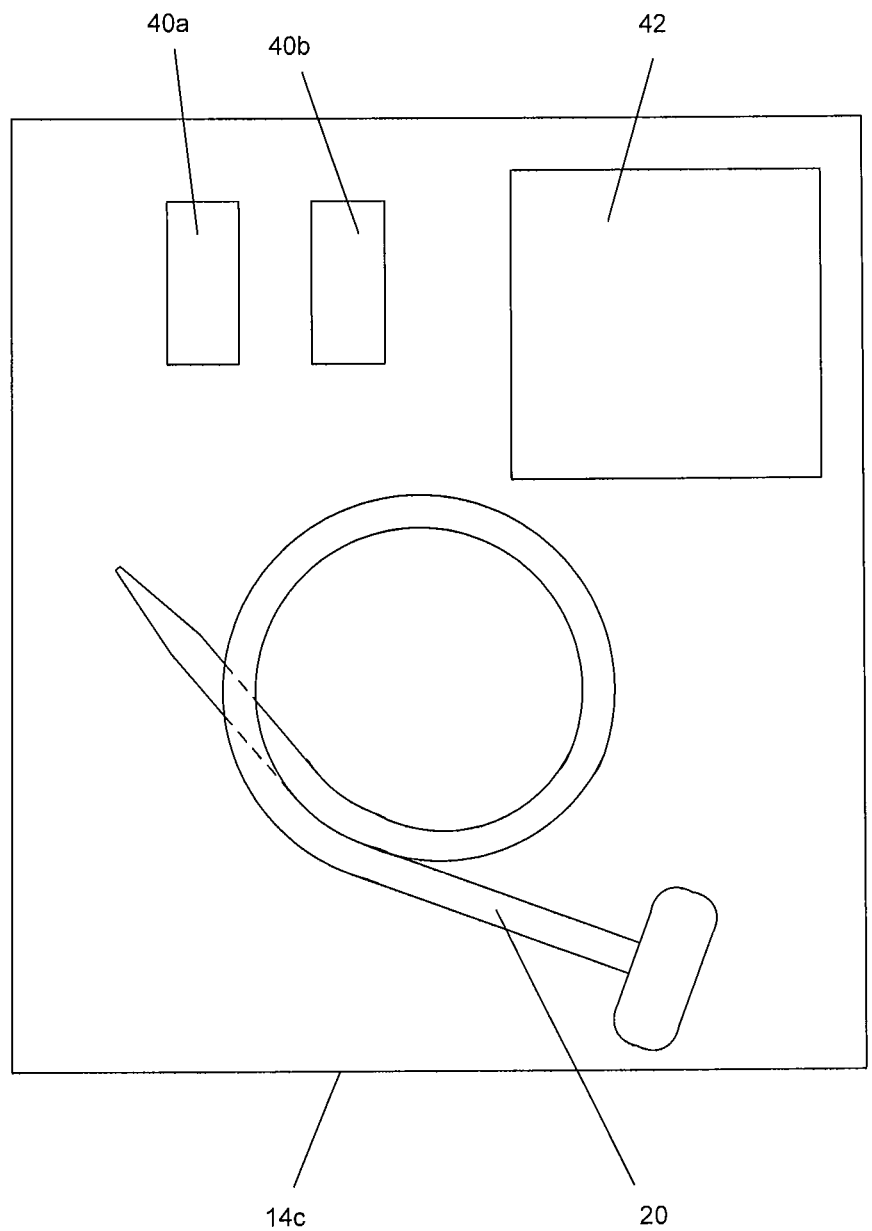
FIG. 4 is a top view of the components inside the third container of the preferred embodiment that relate to the step of inserting the feeding tube.

As shown in FIG. 4, in the preferred embodiment, the third container 14c may contain at least one package of water soluble lubricant 40, where the at least one package of water soluble lubricant 40 preferably comprises two packages 40a, 40b each having three grams of lubricating jelly; at least one gauze pad 42, where the at least one gauze pad 42 preferably comprises five gauze pads 42a-e, and the feeding tube 20.

Figure 5:
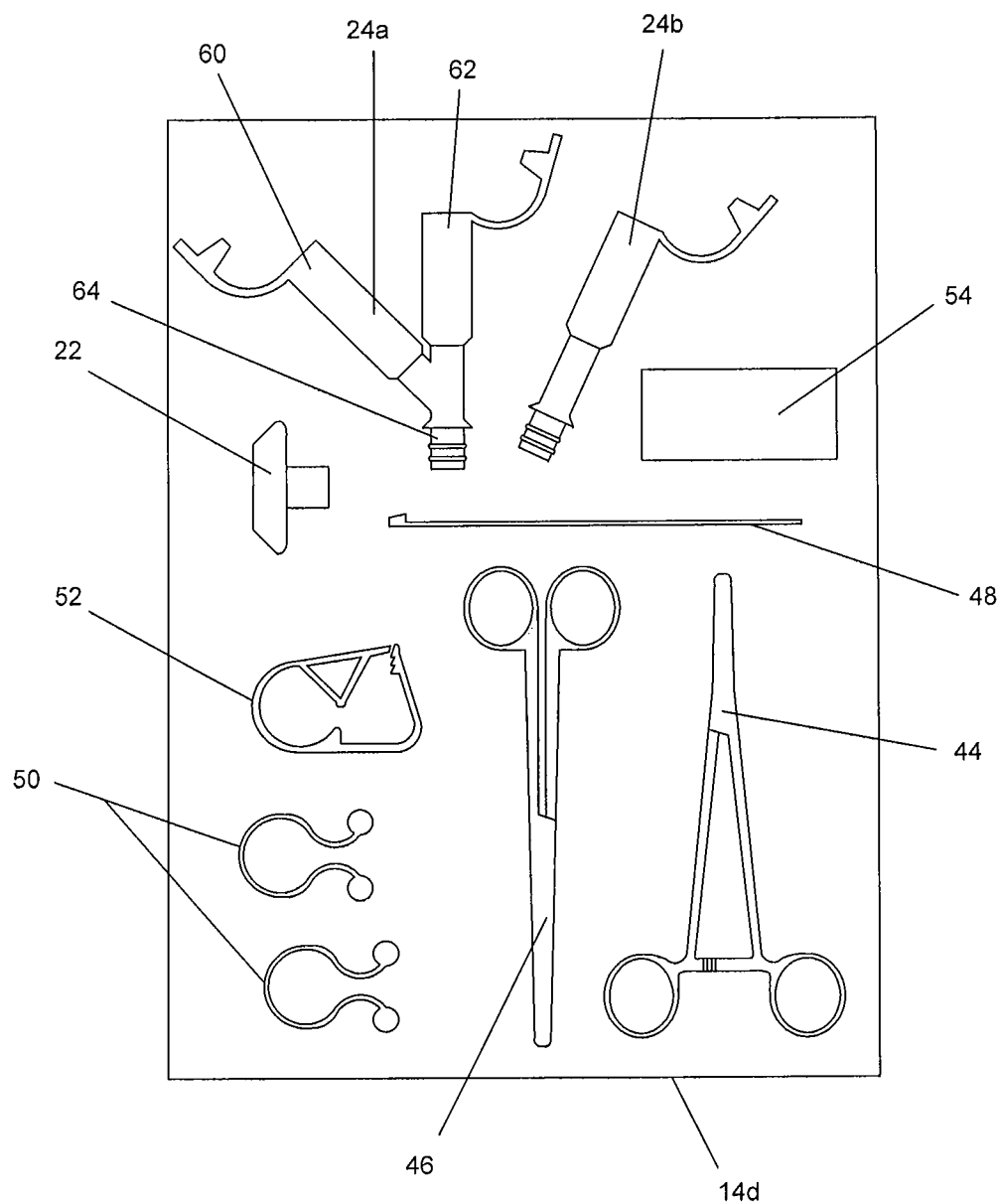
FIG. 5 is a top view of the components inside the fourth container of the preferred embodiment that relate to the step of applying the bolster to the feeding tube, and that relate to the step of attaching the adapter to the feeding tube.

As shown in FIG. 5, in the preferred embodiment, the fourth container 14d may include a universal adapter 24a comprising an input feeding port 60, an input flushing port 62, and an output port 64 for sending material input from either the input feeding port 60 or input flushing port 62 to the feeding tube 20; a bolus adapter 24b; a bolster 22; forceps 44, where the forceps 44 are preferably straight mosquito forceps; scissors 46, where the scissors 46 are preferably five and one-half inch mayo scissors; at least one cable tie 48; at least one twist lock tie 50; and a feeding tube clamp 52, and at least one povidone-iodine package 54.

In the preferred embodiment, as shown in FIG. 1, the containers 14 are attached to the surgical drape 12 around a perimeter 80 of a fenestration site 82. The containers 14 may be attached to the surgical drape 12 in a manner that generally conforms to the shape of the fenestration site 82. For example, as shown in FIG. 1, the fenestration site 82 may have a circular shape, and the containers 14 may be attached around the perimeter 80 in a manner that generally conforms to the circular shape of the fenestration site 82. In addition, the containers 14 may be attached to the surgical drape 12 as close to the fenestration site as possible without the containers 14 covering any portion of the fenestration site 82. Alternatively, some space may exist between the containers 14 and the perimeter 80 of the fenestration site 82. Generally, the containers 14 are attached to the surgical drape 12 as close to the fenestration site 82 as possible without the containers 14 interfering with the surgical procedure. Attaching the containers around the perimeter 80 of the fenestration site 82 in such a manner enables the components 18-54 to be obtained and moved to the fenestration site 82 quickly and easily.

The containers 14 may be sequentially attached to the surgical drape 12 around the perimeter 80 of the fenestration site 82. For example, as shown in FIG. 1, the containers 14 may be sequentially attached around the fenestration site 82 in a clockwise configuration. Using the position of the first container 14a as a position of reference, the first container 14a may be attached to the right of the fenestration site 82, the second container 14b may be attached below the fenestration site 82, the third container 14c may be attached to the left of the fenestration site 82, and the fourth container 14d may be attached above the fenestration site 82.

Alternatively, the containers 14 may be sequentially attached to the surgical drape 12 around the fenestration site 82 in a counter-clockwise configuration. For example, using the position of the first container 14a as a position of reference, the first container 14a may be attached to the right of the fenestration site 82, the second container 14b may be attached above the fenestration site 82, the third container 14c may be attached to the left of the fenestration site 82, and the fourth container 14d may be attached below the fenestration site 82.

In another alternative embodiment, the containers 14 may be non-sequentially attached to the surgical drape 12 around the fenestration site 82. For example, using the position of the first container 14a as a reference position, the first container 14a may be attached to the left of the fenestration site 82, the second container 14b may be attached to the right of the fenestration site 82, the third container 14c may be attached above the fenestration site 82, and the fourth container 14d may be attached below the fenestration site 82.

The containers 14 may be attached to the surgical drape using double-sided tape. An example of double-sided tape that may be used is double coated medical tape having an acrylate adhesive. Alternatively, a plurality of pieces of hook-and-loop fastener material, such as pieces of Velcro®, may be affixed to the surgical drape 12 around the perimeter 80 of the fenestration site 82, and similarly, pieces of hook-and-loop fastener material may be affixed to each of the containers 14. Each of the containers 14 may be attached to the surgical drape 12 by engaging the hook-and-loop fastener material affixed to each of the containers 14 with the pieces of hook-and-loop fastener material attached to the surgical drape 12.

Figure 6:
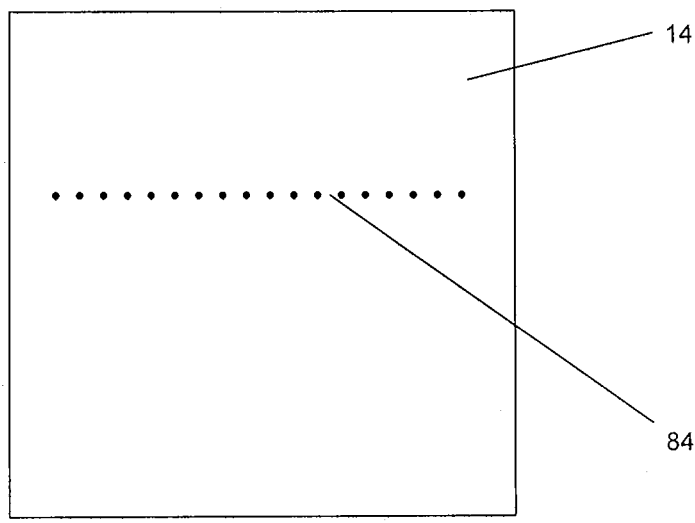
FIG. 6 is a top view of a container, having a perforation.

In the preferred embodiment, the containers 14 may be bags that are transparent and made of plastic. As shown in FIG. 6, each bag 14 may comprise a perforation 84. The perforation 84 of the bag 14 allows for the components 18-54 to be securely contained within the bag 14 prior to the components 18-54 needing to be used. In addition, the perforation 84 allows for easy creation of an opening in the bag in order to easily access the components 18-54 within the bags 14.

Figure 7:
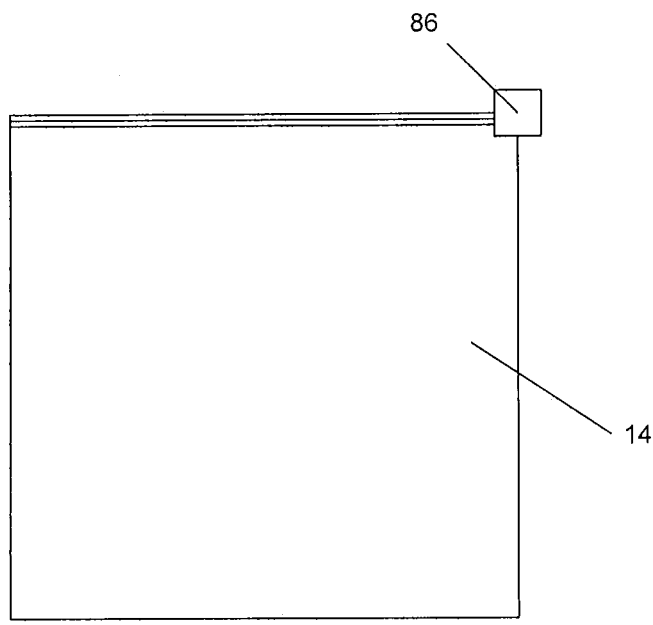
FIG. 7 is a top view of a container, having a sealing mechanism.

Alternatively, the containers 14 may be resealable bags that comprise a sealing mechanism 86 which allows for the bags 14 to be opened to obtain a component 18-54, and then to be resealed. For example, as shown in FIG. 7, the sealing mechanism may be a zipper used in zipper storage bags. A transparent plastic bag 14 having a perforation 84, and a transparent plastic bag having a sealing mechanism 86 are two examples of a container that may be attached to the surgical drape kit 10 to contain the components 18-54 of the PEG procedure, and one of ordinary skill in the art may recognize that other types of similarly operable containers may be used in replace of or in combination with a bag 14 having a perforation 84, and/or a bag 14 having a sealing mechanism 86.

Figure 8:
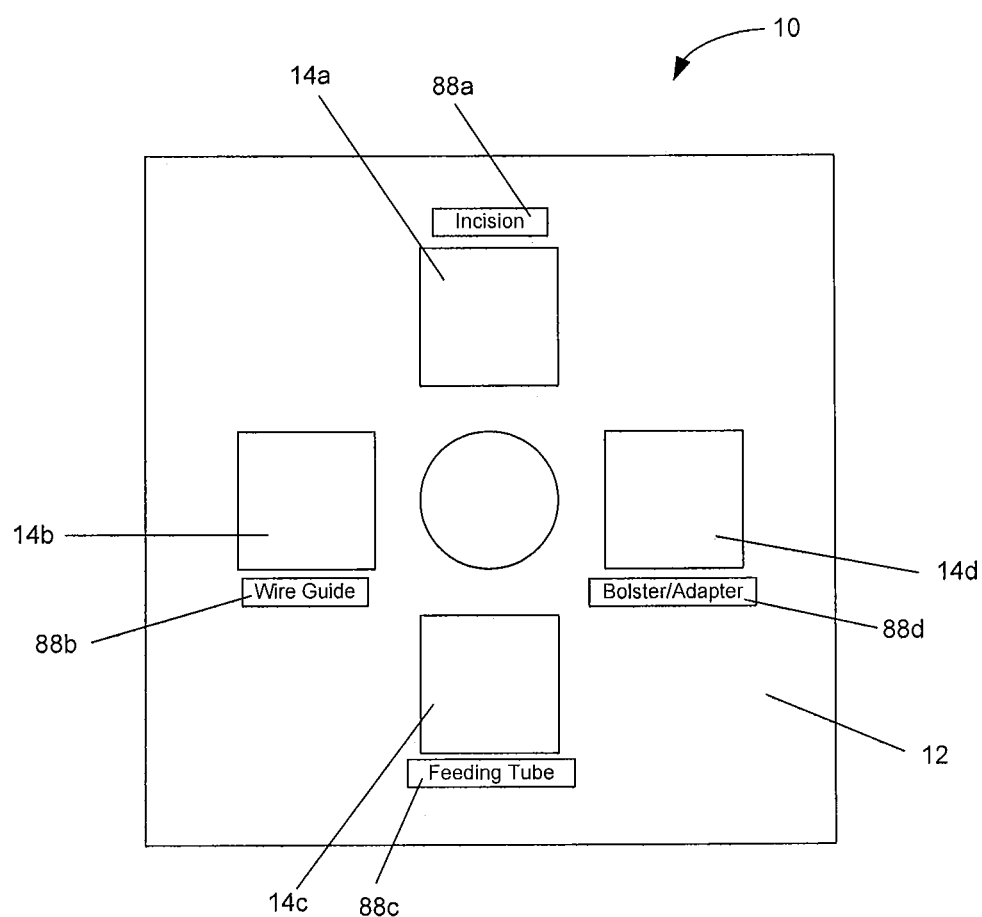
FIG. 8 is a top view of a surgical drape kit, having labels that describe the part of the procedure for which the components inside a particular container will be used, the labels being attached to the surgical drape near the container with which they are associated.

The surgical drape kit 10 further comprises labels 88 to indicate which components 18-54 are in which container 14. As shown in FIG. 1, the labels 88 may be attached to the containers 14. The number of labels 88 corresponds to the numbers of containers 14. Alternatively, as shown in FIG. 8, the labels 88 are attached to the surgical drape 12 near the containers 14.

In order to indicate which components 18-54 are in which container 14, the labels 88 may comprise numbers. For example, in the preferred embodiment as shown in FIG. 1, because there are four containers 14, a first label 88a is numbered one, a second label 88b is numbered two, a third label 88c is numbered three, and a fourth label 88d is numbered four.

Alternatively, the labels 88 may comprise words or symbols that indicate the part of the procedure for which the components inside a particular container will be used. For example, as shown in FIG. 8, the components used to make the incision may be placed in the first container 14a, and a first label 88a may be labeled: "Incision." Likewise, the components used to insert the wire 18 into the patient for enabling insertion of the feeding tube 20 into the patient may be placed in the second container 14b, and a second label 88b may be labeled "Wire Guide" or "Insertion Wire." The components used to insert the feeding tube 20 into the patient may be placed in the third container 14c, and a third label 88c may be labeled "Feeding Tube." The components used to apply the bolster 22 to the feeding tube 20 and the components used to attach an adapter 24 to the feeding tube 20 may be placed in the fourth container 14d, and a fourth label 88d may be labeled "Bolster/Adapter."

As shown in FIG. 1, the fenestration site 82 of the surgical drape 12 may be a circular opening of the surgical drape 12 that allows access to the patient in order for the procedure to be performed. An adhesive coating may be applied to an underside of the drape, and around the perimeter of the fenestration site 82, in order to secure the drape 12 to the patient during the PEG procedure. Additionally, the drape 12 may be made of an absorbent material in order to absorb blood and other fluids during surgery.

The surgical drape kit 10 may be packaged using a pouch-type packaging. The pouch may be made of a variety of materials as understood by one having ordinary skill in the art. Such materials may include, but are not limited to, polyvinyl chloride, polyethylene, polyolefin, polypropylene, polyester, plastic, or paper.

When packaging the surgical drape kit 10, the surgical drape kit 10 may be folded. After the surgical drape kit 10 is folded, but before the folded surgical drape kit 10 is placed inside the packaging, a package of swab sticks 56 may be attached to a side of the folded surgical drape 12. When a user of the surgical drape kit 10 receives the packaged surgical drape kit 10 and removes the surgical drape kit 10 from the pouch, the user may detach the package of swab sticks 56 from the surgical drape 12 before unfolding the packaged surgical drape kit 10. Alternatively, the package of swab sticks 56 may be attached to the surgical drape 12 before the surgical drape kit 10 is folded. When a user of the surgical drape kit 10 removes the surgical drape kit 10 from the pouch, the user may unfold the surgical drape kit 10 and place the surgical drape 12 over the patient before detaching the package of swab sticks 56 from the surgical drape 12.

The arrangement of the PEG procedure components 18-54 inside the containers 14 may be determined prior to the surgical drape kit 10 being packaged and sent to an end user who performs the PEG procedure. Also, prior to the surgical drape kit 10 being packaged and sent to the end user, the containers 14 are attached to the surgical drape 12. Thus, when the end user receives the packaged surgical drape kit 10, the end user may remove from the package the surgical drape 12 having the containers 14 attached to the drape 12, with the components 18-54 being disposed inside the containers 14 according to the determined arrangement.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

I claim:

1. A surgical drape kit for performing a surgical procedure on a patient comprising:
    a surgical drape having a fenestration site;
    a plurality of containers attached to the surgical drape around a perimeter of the fenestration site, each of the plurality of containers having disposed therein at least one of a plurality of components used to perform a surgical procedure, wherein the plurality of components, while disposed in the plurality of containers, has not been previously handled by a performer of the surgical procedure, and wherein each of the containers comprises a series of perforations or a sealing mechanism that securely contain or seal the plurality of components in the plurality of containers when the components have not been previously handled by the performer, and that allow for creation of openings in the plurality of containers to access the plurality of components disposed therein,
    wherein the plurality of components are dividedly and sequentially disposed inside the plurality of containers according to predetermined sequentially divided steps of the surgical procedure.

2. The surgical drape kit of claim 1, wherein the surgical procedure is a percutaneous endoscopic gastrostomy (PEG) procedure, and the plurality of components comprises a plurality of components for performing the PEG procedure.

3. The surgical drape kit of claim 2, wherein the predetermined sequentially divided steps of the PEG procedure comprise:
    making an incision;
    inserting a wire into the patient for enabling insertion of a feeding tube into the patient;
    inserting the feeding tube into the patient;
    applying a bolster to the feeding tube; and
    attaching an adapter to the feeding tube; and
    wherein the plurality of components comprises:
    at least one component related to making the incision;
    at least one component related to inserting the wire into the patient for enabling insertion of the feeding tube into the patient;
    at least one component related to inserting the feeding tube;
    at least one component related to applying the bolster to the feeding tube; and
    at least one component related to attaching the adapter to the feeding tube.

4. The surgical drape kit of claim 3, wherein the plurality of containers comprises: a first container that includes the at least one component related to making the incision disposed inside the first container,
    a second container that includes the at least one component related to inserting the wire into the patient for enabling insertion of the feeding tube into the patient disposed inside the second container;
    a third container that includes the at least one component related to inserting the feeding tube disposed inside the third container; and
    a fourth container that includes the at least one component related to applying the bolster to the feeding tube disposed inside the fourth container, and the at least one component related to attaching the adapter to the feeding tube disposed inside the fourth container.

5. The surgical drape kit of claim 4, wherein the at least one component related to making the incision comprises a scalpel.

6. The surgical drape kit of claim 5, wherein the at least one component related making the incision further comprises at least one of a syringe, at least one needle, and a container of lidocaine hydrochloride.

7. The surgical drape kit of claim 4, wherein the at least one component related to inserting the wire into the patient for enabling insertion of the feeding tube into the patient comprises one of a wire guide and an insertion wire having a looped end,
    wherein the one of the wire guide and the insertion wire having the looped end comprises the wire guide when a push technique is used to perform the PEG procedure; and wherein the one of the wire guide and the insertion wire having the looped end comprises the insertion wire having the looped end when a pull technique is used to perform the PEG procedure.

8. The surgical drape kit of claim 7, wherein the at least one component related to inserting the wire into the patient for enabling insertion of the feeding tube into the patient further comprises at least one of a cold snare, and a needle cannula.

9. The surgical drape kit of claim 4, wherein the at least one component related to inserting the feeding tube comprises the feeding tube.

10. The surgical drape kit of claim 9, wherein the at least one component related to inserting the feeding tube further comprises at least one of at least one package of water soluble lubricant, and at least one gauze pad.

11. The surgical drape kit of claim 4, wherein the at least one component related to attaching the adapter to the feeding tube comprises at least one of a universal adapter and a bolus adapter.

12. The surgical drape kit of claim 11, wherein the at least one component related to attaching the adapter to the feeding tube further comprises at least one of forceps, scissors, at least one cable tie, at least one package of povidone ointment, at least one twist lock tie, and a feeding tube clamp.

13. The surgical drape kit of claim 4, wherein the at least one component related to applying the bolster to the feeding tube comprises the bolster.

14. The surgical drape kit of claim 1, wherein the plurality of containers is sequentially attached to the surgical drape around the perimeter of the fenestration site according to the predetermined sequentially divided steps of the surgical procedure.

15. The surgical drape kit of claim 1, wherein the predetermined sequentially divided steps of the surgical procedure comprises a first step, and a second step;
    wherein the plurality of components comprises a first component used to perform the first step, and a second component used to perform the second step; and
    wherein the plurality of containers comprises a first container that includes the first component disposed therein, and a second container that includes the second component disposed therein.

16. The surgical drape kit of claim 1, wherein the plurality of containers comprises plastic bags.

17. The surgical drape kit of claim 1, further comprising a plurality of labels associated with the plurality of containers,
    wherein each of the plurality of labels comprises at least one of:
        a number that corresponds to a step of the surgical procedure, and
        at least one word that describes a step of the surgical procedure.

18. The surgical drape kit of claim 1, further comprising a package containing the surgical drape, the plurality of containers, and the plurality of components,
    wherein the package is a pouch-type package.

* * * * *

UNITED STATES PATENT AND TRADEMARK OFFICE
CERTIFICATE OF CORRECTION

PATENT NO. : 9,486,293 B2
APPLICATION NO. : 13/097784
DATED : November 8, 2016
INVENTOR(S) : Andrye McCollough It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 335 days.

Signed and Sealed this
Twenty-fifth Day of September, 2018

Andrei Iancu
*Director of the United States Patent and Trademark Office*